United States Patent [19]

Snaper et al.

[11] Patent Number: 4,485,442
[45] Date of Patent: Nov. 27, 1984

[54] CUMULATIVE EXPOSURE METERING SYSTEM

[76] Inventors: Alvin A. Snaper, 2800 Cameo Cir., Las Vegas, Nev. 89107; Stephen Bortniak, 2109 NE. 138th St., Vancouver, Wash. 98665

[21] Appl. No.: 305,182

[22] Filed: Sep. 24, 1981

[51] Int. Cl.³ .................. G06F 15/42; G06G 7/54
[52] U.S. Cl. ................................ 364/414; 364/527; 364/555; 377/11; 377/15; 377/20; 377/26; 250/336.1
[58] Field of Search ............ 364/414, 527, 555; 377/11, 15, 19, 20, 25, 26; 340/347 AD; 250/336.1, 374, 372, 392

[56] References Cited

U.S. PATENT DOCUMENTS

| | | | |
|---|---|---|---|
| 2,845,530 | 7/1958 | Wade | 377/11 |
| 2,874,899 | 2/1959 | Roehrig | 377/11 |
| 2,927,217 | 3/1960 | Vacca | 377/11 |
| 3,153,727 | 10/1964 | Nathan | 377/11 |
| 3,390,229 | 6/1968 | Williams | 377/11 |
| 3,390,230 | 12/1975 | Stephens | 377/11 |
| 3,705,383 | 12/1972 | Frayer | 377/10 |
| 3,932,839 | 1/1976 | Stephens | 377/11 |
| 3,935,562 | 1/1976 | Stephens | 377/11 |
| 4,240,107 | 12/1980 | Yoshida | 377/11 |

Primary Examiner—Errol A. Krass
Assistant Examiner—Clifford L. Tager

[57] ABSTRACT

An electron dosimeter system which measures the length of time that an individual, or object, is exposed to discrete strength levels of a stimulating medium. The dosimeter device is comprised of a sensing device with associated electronics, a converter and a processing circuit. The sensing device/electronics produces an electrical output, representing the strength level of the stimulating medium, which is converted to electrical pulses. The output of the converter is comprised of electrical impulses whose frequency or repetition rate represents the strength of the stimulating medium. The output of the converter is then processed in a circuit having a plurality of storage devices, each of which represent a discrete strength level of the stimulating medium. The processor produces a plurality of timed interval pulses which are addressed to the particular storage device representing that strength level of the stimulating medium. An external and separate reader with display can be plugged into the processing circuit for reading the time interval of a particular strength level in any of the storage devices, when desired.

9 Claims, 4 Drawing Figures

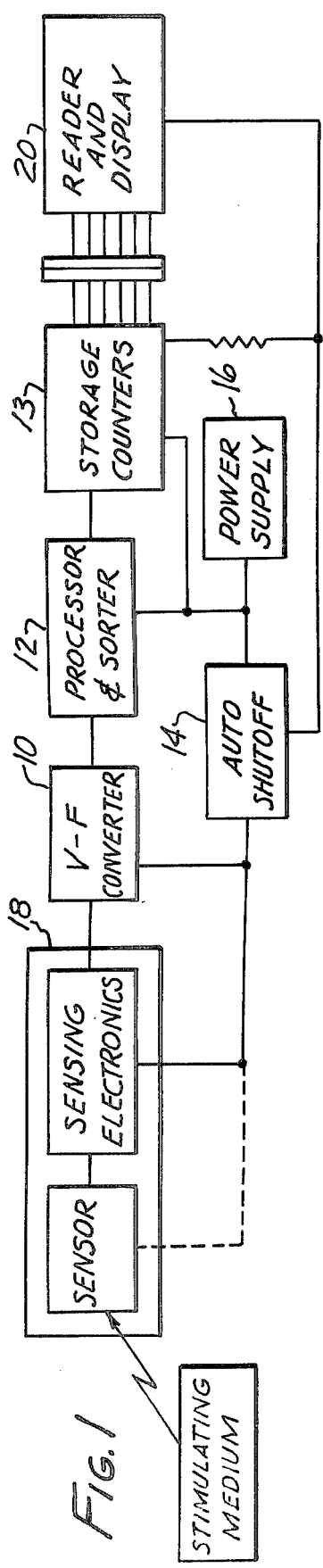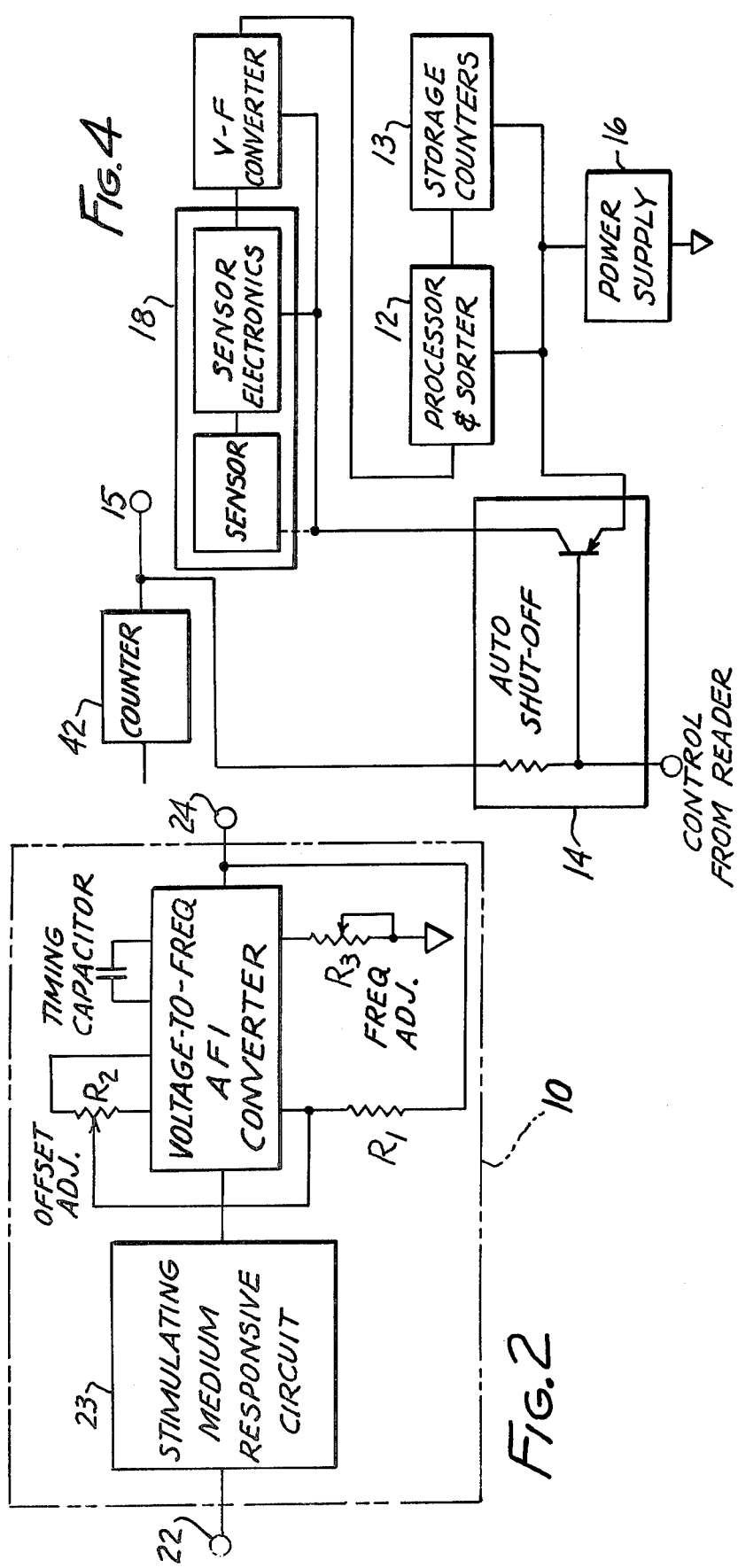

CUMULATIVE EXPOSURE METERING SYSTEM

FIELD OF THE INVENTION

This invention relates to dosimeter devices which measure the cumulative exposure to a stimulating medium such as radiation, noise, light or other media.

In present dosimeter devices cumulative exposure to a particular stimulating medium is read by a sensing plate which is usually designed to indicate when the cumulative exposure exceeds a predetermined amount. These devices do not provide a true indication of the intensity or time of exposure to the stimulating medium at a given intensity. In one such device a photographic film plate is used for measuring exposure to radiation and is worn by a person who might encounter this type of stimuli. The cumulative effects of the radiation are stored by photographic film which darkens with the amount of exposure, and thereby is a measure of the amount of stimulus the wearer has been subjected to.

While these devices are effective to provide an indication of the cumulative amount of a stimulating medium, they are not very informative as to the particular strength levels or time of exposure at a given level. It would be advantageous if exposure time, at particular strength levels to various stimulating sources such as nuclear, electro-magnetic or solar radiations, sound levels, chemical vapors, psychological reactions (heart rate, blood pressure, temperature), mechanical phenomena (shock, vibration, acceleration), or other stimuli, could be measured and recorded so that the effects or values of these stimuli can be meaningfully interpreted.

SUMMARY OF THE INVENTION

The purpose of the present invention is to provide a exposure metering system which measures and stores exposure time to discrete strength levels of a stimulating medium.

The exposure metering system of the present invention is comprised of integrated circuit devices interconnected in such a manner and interfaced with a sensing device which senses the particular stimuli and can measure and store the exposure time to discrete strength levels. A device with applicable electronics responsive to the stimulus produces an electrical signal indicating the strength level which is fed to an analog-to-frequency (or voltage-to-frequency) converter. The electrical signal is then amplified and converted to electrical pulses whose frequency (or repetition rate) represents the strength of the stimulating medium. The electrical pulses are then fed to a processor which produces time interval signals which are addressed to selected storage devices according to the discrete strength level sensed. The timed interval pulses are addressed to a storage device by sensing the frequency of the signal from the converting circuit representing the discrete strength level. As long as the output from the converting circuit continues at the same average frequency, timed interval pulses will continue to be addressed to the storage device selected.

The processor is comprised of a digital, integrated circuit (such as those presently available for electrical counting, multiplex, digital logic and multivibrator application) interconnected in such a manner that the measurement of exposure time to the discrete strength levels of the stimulus can be recorded. The number of strength levels being measured and stored is limited only by the number of integrated circuit devices needed to achieve a desired dosimeter capacity. The exposure metering system also includes shut-off provisions to prevent exceeding the capacity of the storage circuits. Signals generated by the sensing and timing circuits are disabled when maximum storage capacity of the storage devices is reached. The exposure time at each of the discrete strength levels can be determined by connecting an external and separate readout and display device which interrogates the storage devices. If the storage devices are interrogated before an automatic shut-off condition has been reached and it is pertinent to know the actual time that monitoring has been in effect, (i.e., total running time) means are provided for storing the total running time.

An overflow inhibit circuit is also provided in the digital processor to prevent false counts from being counted when an overrange (i.e., excessive strength levels) condition exists. The processing circuit is disabled when an overrange condition exists by inhibiting timing circuit signals. The period during which an overrange condition existed can be determined by substracting the total exposure time in the storage devices from the total running time of the processing circuit.

OBJECTS OF THE INVENTION

It is one object of the present invention to provide an electronic exposure metering system which measures the time of exposure to discrete strength levels of a stimulating medium.

Another object of the present invention is to provide an electronic exposure metering system which converts an electrical signal representing discrete strength levels to electrical pulses having a frequency representing the discrete strength level.

Still another object of the present invention is to provide an electrical exposure metering system which measures and stores the exposure time at discrete strength levels of a stimulating medium.

Still another object of the present invention is to provide an electrical exposure metering system which has a clocking circuit for producing timed interval signals which are inserted in storage devices which represent discrete strength levels of exposure to a stimulating medium.

Still another object of the present invention is to provide an electronic exposure metering system which prevents erroneous readout operations by disabling processing circuits when the capacity of the storage devices is exceeded.

Yet another object of the present invention to to provide an electronic exposure metering system which prevents overrange errors by sensing an overrange condition and inhibiting timing circuit signals.

These and other objects of the invention become obvious from the following detailed description and when considered in conjunction with the accompanying drawings, in which:

BRIEF DESCRIPTION OF THE DRAWINGS

FIG. 1 is a block diagram of the electronic exposure metering system;

FIG. 2 is a schematic diagram of the converting circuit of FIG. 1;

FIG. 4 is a schematic diagram illustrating operation of the automatic shut-off circuit.

DETAILED DESCRIPTION OF THE INVENTION

Figure 3:
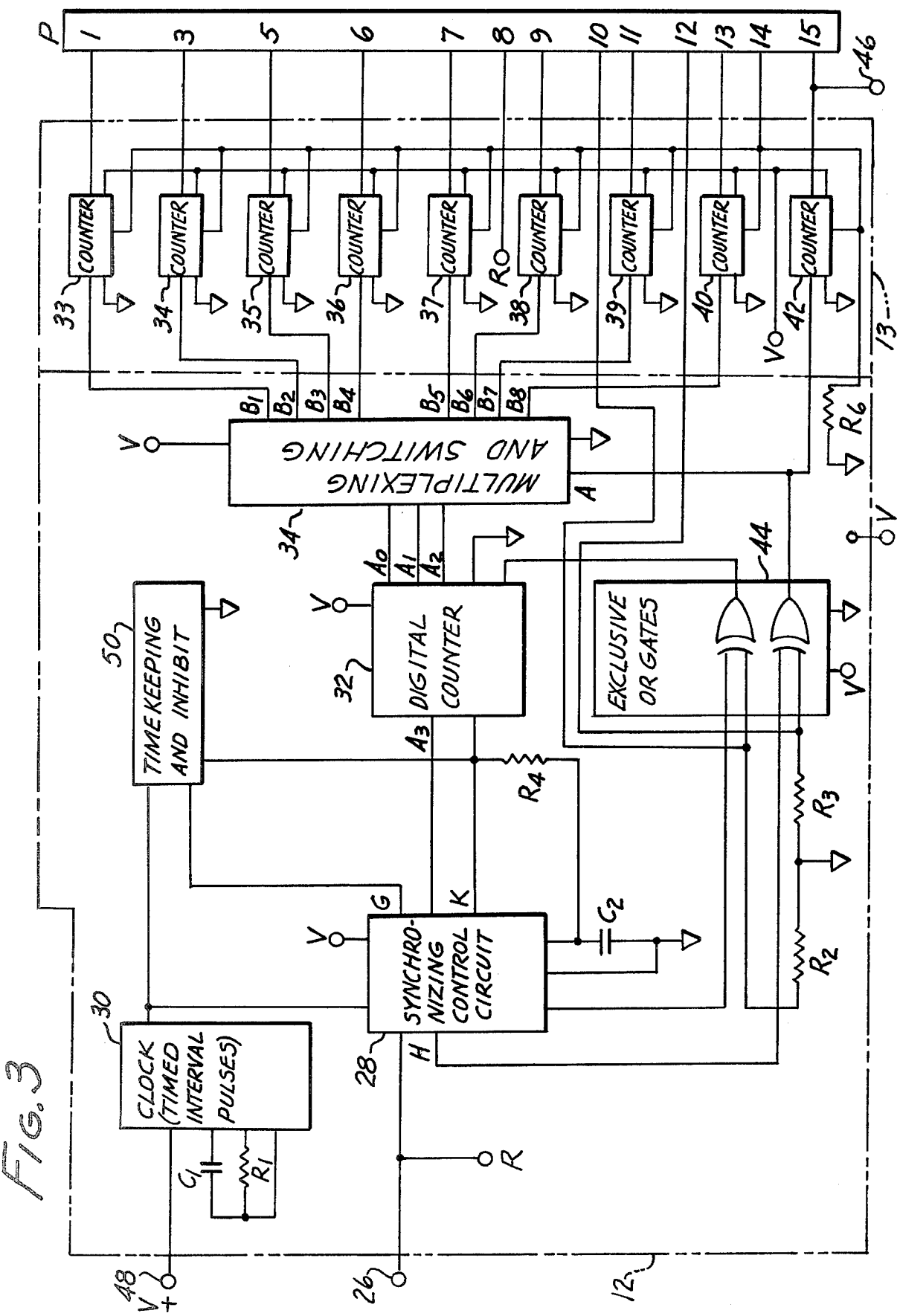
FIG. 3 is a schematic diagram of the processing and storage circuit of the electronic exposure metering system.

The exposure metering system shown in FIG. 1 is comprised of a converter circuit 10, a processing circuit 12, storage circuits 13, an automatic disabling or shut-off circuit 14, and a power supply 16. The exposure metering system receives an input from some type of sensing device and associated electronics 18 which produces an electrical output representing exposure to a stimulating medium. The dosage processed by the exposure metering system is interpreted and displayed by a separate reader and display 20 which interrogates the storage devices 13 via the processing circuit 12.

The sensing device 18 comprised of a sensor and associated electronics converts the stimulating medium to an electrical signal which is fed to the converting circuit 10. The converting circuit 10 converts the electrical signal to electrical impulses whose frequency (or repetition rate) represents the strength of the stimulating medium to which the sensing device 18 is exposed and is shown in the schematic of FIG. 2. The output from the sensing device 18 is received by the converting circuit 10 at terminal 22 and is transferred by stimulating medium response circuit 23 to the voltage to frequency (or analog to frequency) converter AF1. The stimulating medium response circuit 23 will change in design with the medium to be measured. In the case of electric field or other AC type signal sensors, operational amplifiers will be used. The resistors R1, R2 and R3 will also change with the type of voltage to frequency converter used. However, the concept of frequency adjustment, offset adjustment, and a timing capacitor will be typical. The voltage to frequency converter may not be necessary if a pulse-producing sensor such as a geiger tube is used. The converter output at terminal 24 will have a frequency or repetition rate representing the strength level of the stimulating medium received by the sensing device 18.

The sensing device 18 will include an appropriate sensor which will vary with the nature of the medium which may include a variety of devices and associated sensing electronics. The main requirement of the sensor is the conversion of a reaction to a stimulating medium to electrical pulses. Examples of appropriate sensors are:

1. A plate or wire antenna responsive to electric and electro-magnetic fields. (Ferrite core antennas and Hall-effect devices can be used).
2. Sound responsive devices (audible, sub-sonic or ultrasonic) such as microphones of various constructions and pressure transducers.
3. Photocells, photodiode, and phototransistors responsive to solar, or other visible and invisible light measurements with appropriate filters and lenses.
4. Chemically reactive devices for chemical vapors such as electrolytic reactions, chemiluminescence, temperature or pressure can be converted to an electrical output.
5. Devices responsive to mechanical forces such as accelerometers, strain gauges, or Bourdon tubes and piezoelectric materials can be converted to a useful electrical output.
6. Devices responsive to nuclear mediums such as geiger tubes may also be used.
7. Devices responsive to temperature such as thermistors, temperature-sensitive semi-conductors, and resistance thermometers.

The associated sensing electronic circuitry will depend on the particular sensor chosen according to the stimulating medium being metered. The main requirement of the associated sensing electronics is that it be able to convert sensor reactions to an adequate electrical output which will operate voltage-to-frequency or analog-to-digital converters. A second requirement of associated sensing electronics is the ability to provide selectivity to a particular spectrum of the stimulating medium (when selectivity is not inherent in the sensor itself). Thus the sensing electronics will employ amplifiers to boost signal levels to a useable output, electric filters, tuned circuits and time constants to reject unwanted signals and utilize excitation circuits to provide conversion of mechanical light and electrical resistance changes to useful electric outputs. Examples of associated sensing electronic circuitry for utilization with particular sensors are:

1. Amplification and selectivity electronics necessary if the sensor is a radio antenna which produces an electrical output.
2. Amplification circuits for use with piezoelectric crystals, when pressure is applied, whose output sometimes can be used directly. If a particular frequency is to be observed, the electronics will include tuned circuits and filters.
3. A circuit which will provide excitation voltages as well as amplifiers and selectivity circuits for use with strain gauges whose electric resistance changes with the stimulating medium.
4. Pressure and resistance devices responsive to mechanical actuation for converting the mechanical change of a Bourdon tube to an electrical output.
5. An electronic source of high voltage to power a geigermuller tube to generate pulses. The pulses generated can either be used directly or by an electronic processor.

The converter output is connected to the input 26 of the processing and sorting circuit 12 shown in the schematic block diagram of FIG. 3. The input at 26 is applied to the synchronizing control circuit 28 which also receives an input of timed interval pulses from clock circuit 30. The output of the synchronized control circuit 28 is connected to the digital counter 32 at $A_3$ which produces electrical outputs at $A_0$, $A_1$ and $A_2$ which change according to the number of pulses applied and length of pulse train applied at $A_3$ at the end of a given time interval determined by the number of pulses received from clock 30. The output $A_0$, $A_1$ and $A_2$ of the digital counter 32 are connected to addressing inputs of the multiplexing and switching circuit 34. The multiplexing and switching device 34 permits only one output to any one of lines $B_1$ to $B_8$ depending upon the logic states of $A_0$, $A_1$ and $A_2$. The three outputs $A_0$, $A_1$ and $A_2$ provide eight logic states for providing an output to any one of eight counter or storage devices 33-40. According to the logic state of the outputs from the digital counter 32, one of the counters 33-40 is selected and receives timed interval pulses from clock 30 through synchronizing circuit 28 and exclusive OR gates 44 to input A of multiplexing and switching circuit 34. The timed interval pulses from the clock 30 are also simultaneously fed to counter 42 to measure total running time which will also provide an output to prevent erroneous readout due to overflow as will be described in greater detail hereinafter. The timed interval pulses received at the input A of the multiplexing and switching circuits directed to one of the counters 33-40 advances that counter by one count.

The storage counters 33 through 42 as used in the present system indicate exposure time in decrete "windows" or steps of the total range being measured.
Counter 33 reads 0-1 units of stimulus strength
Counter 34 reads 1-2 units of stimulus strength
Counter 35 reads 2-3 units of stimulus strength
Counter 36 reads 3-4 units of stimulus strength
Counter 37 reads 4-5 units of stimulus strength
Counter 38 reads 5-6 units of stimulus strength
Counter 39 reads 6-7 units of stimulus strength
Counter 40 reads 7-8 units of stimulus strength
Counter 42 reads 0 to infinity units of stimulus strength To determine exposure time at strengths above 8 units the counts are totalled for counters 33 through 40 and substracted from the counts in counter 42. If the strength of the stimulating medium falls between 4 and 5 units, only counter 37 will advance one count. Thus, counter 42 will also advance one count as it will whenever any of the other counters 33 through 40 advance. After a count is entered, the digital counter 32 is automatically reset to zero and the process described above repeated. At the end of the next timed interval, a pulse is again applied to point A of the multiplexing and switching circuit 34 again advancing the count in one of the counters 33-40. The selection of the counter provided by the processing circuit is directly proportional or representative of the strength of the stimulating medium. This process is continued indefinitely until stopped by manual or automatic means. The number of counts received by a particular counter represents the time of exposure to the strength level of the stimulating medium represented by that counter.

To prevent overflow and erroneous readouts, as well as recording the total running time, a counter 42 generates an automatic disabling signal. Since the counting capacity of the counters 33-40 is limited, it is necessary to include means to shut off the monitoring when the maximum counting capacity is reached. This is achieved through counter 42 as illustrated in FIG. 4. Pulses generated by the clock circuit 30 are applied through exclusive OR gates 44 to the counter 42. This counter advances one count with each timed pulse until output at 46 changes electrical state. This change in state activates the automatic shut off circuit 14 disabling the converter circuit 10 sensing electronics and sensor if powered, cutting off the power applied at 48 to the clock 30, cutting off the sensing and timing circuits and stopping the process described above. The circuit is provided with a direct connecting "keep alive" buss 15 to hold memory and permit readout operations via the processor. To restart the monitoring process after a automatic shut off has occurred a reset pulse is applied through pin 14 of plug P to reset the counters 33-40 and 42.

An overrange inhibit capability is provided because the maximum stimulus strength that can be accepted is limited to a finite level. To prevent false counts being registered, when an overrange condition exists, the output $A_3$ from the digital counter 32 is used as a control to stop the timed interval pulses from reaching the counters 33-40. The output $A_3$ from digital counter 32 changes state when the stimulating medium exceeds the limit of the processing circuit. This change in state disables the synchronizing control circuit 28 and the multiplexing and switching circuit 34 preventing counters 33-40 from being advanced by the timing circuit pulses. The counter 42, however, continues to advance with each timed pulse. The time spent in overrange conditions can be determined by subtracting the sum total exposure times in counters 33-40 from the total running time shown by the counter 42.

Time keeping is provided by the clock circuit 30 which is an astable multivibrator used to generate the timed intervaled pulses needed to place counts in counters 33-40. The time keeping and inhibit circuit 50 is used to achieve long sample times not possible with the clock circuit alone and to inhibit the synchronized control circuit 28 action during both measurement and counting operations. An inhibit pulse from the inhibit circuit 50 is applied to the synchronizing control circuit 28 at G, inhibiting the actions of the processing circuits during both measurement and counting operations. When the inhibiting signal G is removed, a pulse appears first at H, which via exclusive OR gates 44 and multiplexing circuit 34, places a count in one of the counters 33-40. This is then followed by a pulse at K which resets the digital counter 32 and timekeeping and inhibit circuit 50 back to the starting points. (The resistor R4 and capacitor C2 allow the latter circuits to be firmly reset before the synchronizing control circuit 22 itself is reset). When reset is accomplished, the inhibiting signal is reapplied at G to lock out signals from converter 10 while counting and resetting actions are in progress. The resistors R2, R3 and R6 prevent damage that might occur when inputs are left open circuited. As was stated previously, the power supplied to clock circuit 30 comes from the automatic shut off circuit 14 which allows the clock circuit to be disabled during reading operations or other conditions requiring such action.

Read out is accomplished by connecting a separate reader and display device 20 to the connector P and applying a shut off signal through pin 8 to the auto shut off control circuit 14. Pulses are then applied through pin 10 to the exclusive OR gate 44 and digital counter 32 until $A_0$, $A_1$, $A_3$ logic levels allow access via the multiplex and switching circuit 34 to the counters 33-40. When addressing is obtained, pulses to the digital counter 32 are discontinued. After access to the desired counters is achieved as described above, pulses from an external source (reader) are applied via input 12 to exclusive OR gate 44 and input A of multiplexing and switching circuit until the counter reaches a count that causes the output to change its electrical state. The number of pulses needed to cause a particular counter to change state are counted by an external device whose counting method is controlled by the changes at the output of the counter.

Exposure time may then be determined by the relation of the number of pulses from an external source that must be added to the number of pulses already counted by the process described above and the relation of the combined count to that needed to produce changes in the output of the counter. When reading operations are satisfied, a new monitoring cycle, achieved by applying an electrical pulse through common reset line, and the steps described above are repeated.

This invention is not to be limited by the embodiments shown in the drawings and described in the description, which are given by way of example and not of limitation, but only in accordance with the scope of the appended claims.

We claim:

1. An exposure metering system in which exposure times to discrete strength levels of a radiation medium are recorded comprising:
   sensing means sensing a radiation medium and producing an output voltage;
   converting means receiving and converting said output voltage to a plurality of electrial pulses whose frequency represents a discrete strength level of said stimulating medium;
   processing means for processing the electrical pulses from said converting means, said processing means comprising;
   means for producing pulses having a timed interval;
   logic means combining said timed interval pulses and said plurality of pulses to produce a logic output indicative of said discrete strength level;
   a plurality of storage means, each of said storage means representing a discrete strength level; and
   addressing means receiving said logic output and directing pulses to one of said storage means according to the discrete strength level whereby the number of pulses received by said storage means provides a record of the approximate time period of exposure to the strength level of radiation represented by each of said storage means.

2. The exposure metering system according to claim 1 in which said addressing means includes multiplexing means directing timed interval pulses to one of said storage means according to the output from said logic means.

3. A system according to claim 2 in which said plurality of storage means comprises digital counters for receiving and counting said timed interval pulses.

4. A system according to claim 3 in which said storage means comprises at least eight digital counters.

5. A system according to claim 4 including means for disabling said processing means before any of said storage means reaches an overflow condition.

6. A system according to claim 5 in which said disabling means comprises;
   a counter adapted to receive and count all the timed interval pulses received by said storage means;
   said counter adapted to activate a power shut off circuit when its maximum capacity is reached.

7. A system according to claim 6 including counting means for counting the total running time of said exposure metering system.

8. A system according to claim 4 including inhibit means for inhibiting the operation of said exposure metering in the event of a overrange condition.

9. The system according to claim 8 in which said timed interval pulses are generated by an astable multivibrator.

* * * * *